US00PP28066P3

(12) United States Plant Patent
Suphachadiwong

(10) Patent No.: US PP28,066 P3
(45) Date of Patent: May 30, 2017

(54) ***PHALAENOPSIS* PLANT NAMED 'SUPHAL1401'**

(50) Latin Name: ***Phalaenopsis* Blume**
Varietal Denomination: Suphal1401

(71) Applicant: Thumrong Suphachadiwong, Bangphra (TH)

(72) Inventor: Thumrong Suphachadiwong, Bangphra (TH)

(73) Assignee: Suphatschatwong Innovation Co., Ltd., Bangphra (TH)

( * ) Notice: Subject to any disclaimer, the term of this patent is extended or adjusted under 35 U.S.C. 154(b) by 20 days.

(21) Appl. No.: 14/757,766

(22) Filed: Dec. 23, 2015

(65) Prior Publication Data

US 2016/0192570 P1 Jun. 30, 2016

(30) Foreign Application Priority Data

Dec. 30, 2014 (QZ) ..... PBR 2014/3621

(51) Int. Cl.
*A01H 5/02* (2006.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Samuel R. McCoy, Jr.

(57) ABSTRACT

A new and distinct *Phalaenopsis* cultivar named 'Suphal1401' which is characterized by small flowers with a large portion of the sepal and petal surfaces colored white and overlaid with both dark and light red-purple spots and blotches of irregular size and arrangement, a dark red-purple labellum with a cleft central lobe, and the stability of these characteristics from generation to generation.

3 Drawing Sheets

Latin name of the genus and species: The Latin name of the genus and species of the novel variety disclosed herein is *Phalaenopsis* Blume.

Variety denomination: The inventive variety of *Phalaenopsis* disclosed herein has been given the variety denomination 'Suphal1401'.

CROSS REFERENCE TO RELATED APPLICATIONS

This application claims priority to the Community Plant Variety Rights application number 2014/3621, filed Dec. 30, 2014, which is herein incorporated by reference.

BACKGROUND OF THE INVENTION

Parentage: The *Phalaenopsis* variety 'Suphal1401' is the result of a planned breeding program. The new variety originated as a seedling from the crossing of the unpatented, proprietary seed parent *Phalaenopsis* Blume 'G3S8' with the unpatented, proprietary pollen parent *Phalaenopsis* Blume 'B4P'. Both parents were developed by, and are owned by, the inventor and were never commercially released. The crossing was made by the inventor in his research greenhouse in Chonburi, Thailand in November of 2005.

The new variety was first selected in October of 2008, in a research greenhouse in Chonburi, Thailand belonging to the inventor. After identifying the new variety as a potentially interesting selection, the inventor continued confidential testing and propagation of 'Suphal1401', assessing stability of the unique characteristics of this variety.

Asexual Reproduction: Asexual reproduction of the new cultivar 'Suphal1401', by way of mericloning, was first initiated in October of 2008 at a commercial laboratory belonging to the inventor in Chonburi, Thailand. Access to all plants was restricted, as plants were kept in a greenhouse not open to the public, and tissue culture plantlets were in a laboratory belonging to the inventor, and not accessible to the public. Through four subsequent generations, the unique features of this cultivar have proven to be stable and true to type.

SUMMARY OF THE INVENTION

The cultivar 'Suphal1401' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Suphal1401'. These characteristics in combination distinguish 'Suphal1401' as a new and distinct *Phalaenopsis* cultivar:

1. *Phalaenopsis* 'Suphal1401' exhibits white petals which are contrasted by an irregular color pattern consisting of dark red-purple spots and also blotches of colors ranging from dark red-purple to violet-purple; and
2. *Phalaenopsis* 'Suphal1401' exhibits white lateral sepals which are broadly margined and occasionally dotted red-purple; and
3. *Phalaenopsis* 'Suphal1401' exhibits a white dorsal sepal which is irregularly margined and occasionally dotted red-purple and further contrasted by a broad central stripe of red-purple; and
4. *Phalaenopsis* 'Suphal1401' exhibits a dark red-purple labellum with the central lobe cleft into two strongly incurved projections; and
5. *Phalaenopsis* 'Suphal1401' exhibits small flowers.

BOTANICAL DESCRIPTION OF THE PLANT

Figure 1:
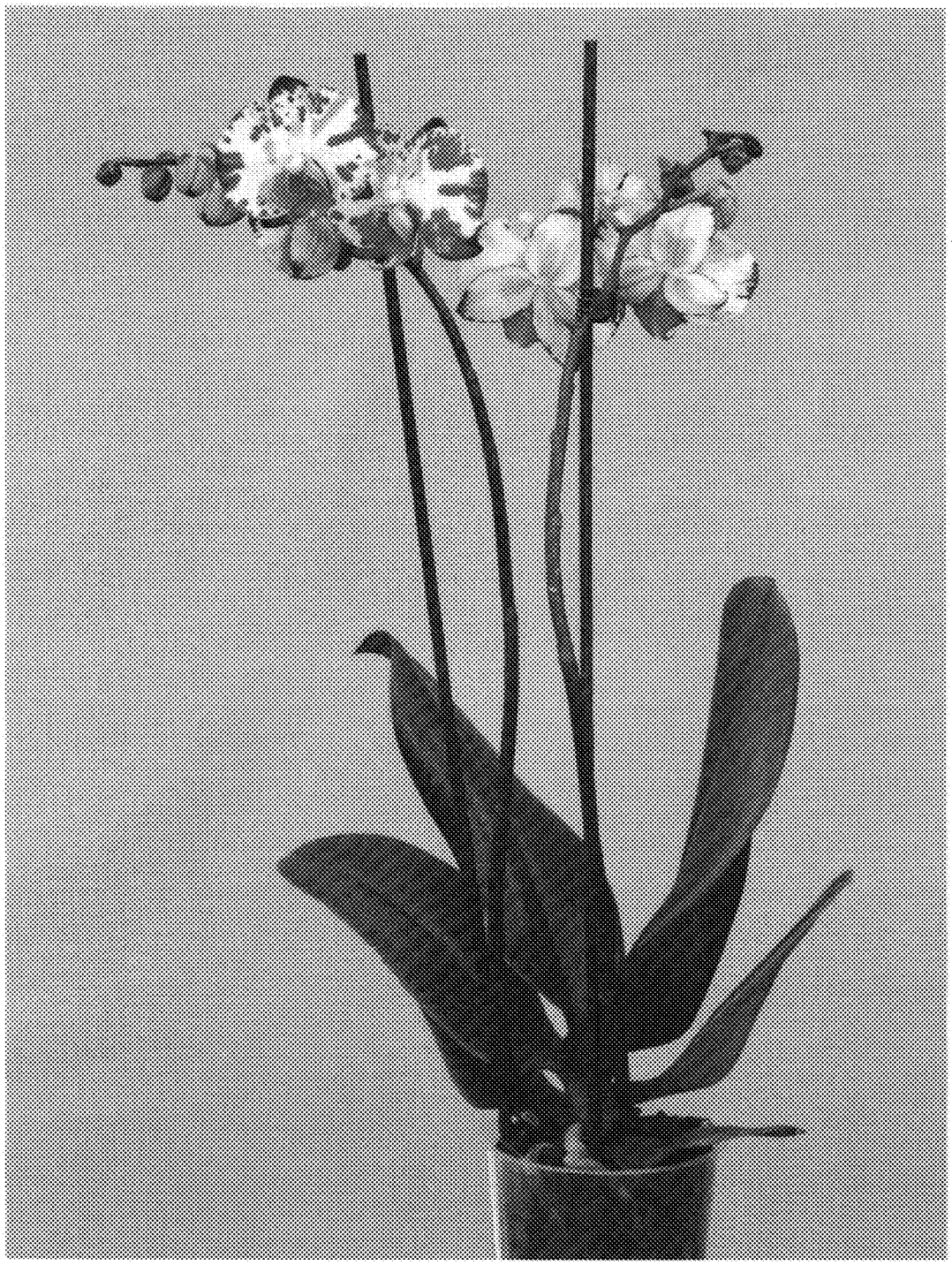
FIG. 1 illustrates, as nearly true as it is reasonably possible to make the same in color photographs of this type, an exemplary plant of 'Suphal1401' grown in a commercial greenhouse in Zuidbroek, the Netherlands. This plant is approximately 12 months old from the time of mericloning, shown planted in a 12 cm nursery container.
Figure 2:
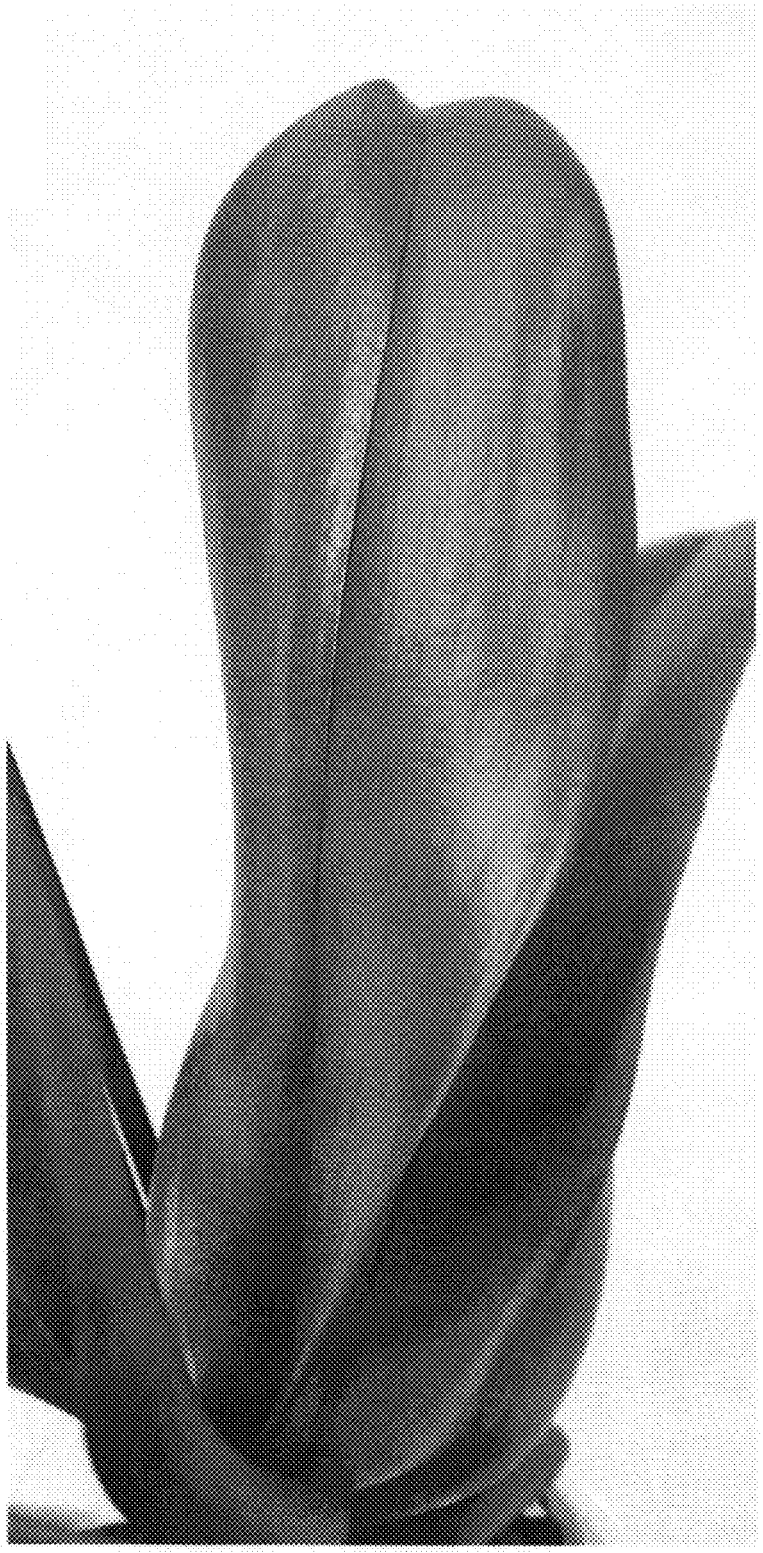
FIG. 2 illustrates, as nearly true as it is reasonably possible to make the same in color photographs of this type, the typical foliage of 'Suphal1401'.
Figure 3:
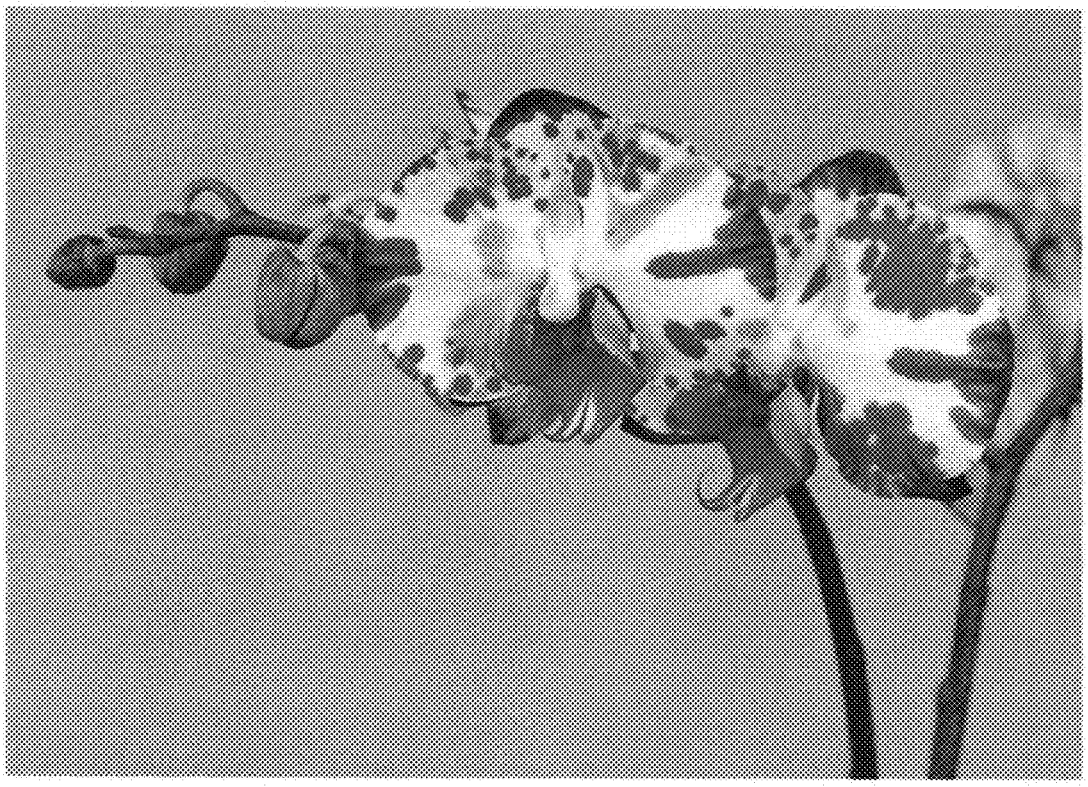
FIG. 3 illustrates, as nearly true as it is reasonably possible to make the same in color photographs of this type, the typical inflorescence of 'Suphal1401'.

The following observations and measurements made in December of 2015 describe averages from a sample set of six specimens of 12 month-old 'Suphal1401' plants grown in 12 cm nursery pots at a greenhouse in Zuidbroek, the Netherlands. Temperatures ranged from approximately 28 degrees Celsius during the day and 18 degrees Celsius at night. No photoperiodic or chemical treatments were given to the plants. During periods of high summer light levels, shade was provided. During the winter months supplemental light was given at unspecified amounts.

Those skilled in the art will appreciate that certain characteristics will vary with older or, conversely, with younger plants. 'Suphal1401' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'Suphal1401' and comparisons with other varieties of *Phalaenopsis* are provided below.

Plant description:

- *Growth habit.*—Perennial; monopodial, upright. Single monopodial basal rosette with inflorescences growing from the leaf axils; flowers are carried above the leaf plane.
- *Average height from base to top of foliar plane.*—21.9 cm.
- *Average height from base to top of floral plane.*—50.2 cm.
- *Plant spread.*—Average of 29.8 cm.
- *Growth rate.*—Moderate.
- *Plant vigor.*—Moderate.
- *Propagation type.*—Mericloning.
- *Time to initiate roots.*—About 21 days at approximately 28 degrees Celsius.
- *Time to produce a rooted cutting/liner.*—About 26 weeks at approximately 18 to 28 degrees Celsius.
- *Disease and pest resistance or susceptibility.*—Similar to other *Phalaenopsis* varieties.
- *Environmental tolerances.*—Adapt to, at least, USDA Zones 11 and 12 and temperatures as high as 40 degrees Celsius; high tolerance to rain; moderate to high tolerance to wind.

Root system:

- *General.*—Moderately dense rooting.
- *Dimensions, mature roots.*—16.8 cm long with a diameter of 0.5 cm, on average.
- *Texture.*—Very fleshy; non-fibrous.
- *Color.*—Green, near RHS 143C.

Stem:

- *Branching habit.*—Monopodial; no lateral branches present.
- *Number of primary stems per plant.*—None; leaves form a basal rosette.
- *Number of secondary branches per plant.*—None.

Foliage:

- *Arrangement.*—Distichous.
- *Dimensions.*—23.3 cm long and 9.1 cm wide, on average.
- *Shape of blade.*—Oblong to long obovate; slightly carinate.
- *Aspect.*—Slightly curved.
- *Apex.*—Unequal acute.
- *Base.*—Sheathing.
- *Sheath dimensions.*—1.8 cm long and 1.4 cm wide, on average.
- *Sheath color.*—Yellow-green, RHS 144B, and slightly darker towards the base, RHS 144A.
- *Margin.*—Entire.
- *Pubescence, texture and luster of adaxial surface.*—Glabrous, smooth, and moderately glossy.
- *Pubescence, texture and luster of abaxial surface.*—Glabrous, smooth, and moderately glossy.
- *Color.*—Juvenile foliage, adaxial surface — Green, near RHS NN137A, to yellow-green, near RHS 147A. Juvenile foliage, abaxial surface — Yellow-green, near RHS 146A, and tinged greyed-purple, RHS N186C. Mature foliage, adaxial surface — Green, near RHS 143A, to yellow-green, near RHS 146B yet darker. Mature foliage, abaxial surface — Yellow-green, near RHS 146A, and tinged greyed-purple, RHS N186C.
- *Venation.*—Parallel.
- *Venation color, adaxial surface.*—Green, near RHS 143A, to yellow-green, near RHS 146B yet darker.
- *Venation color, abaxial surface.*—Green, RHS 143A, and tinged greyed-purple, RHS N186C.
- *Petiole.*—No petioles present, leaves are sessile.

Inflorescence:

- *Inflorescence arrangement.*—Axially placed raceme.
- *Natural flowering season.*—Autumn into winter.
- *Time to flower.*—Approximately 10 months.
- *Flowers per inflorescence.*—Average of 18; 6 open flowers and 12 buds.
- *Height.*—Approximately 16.4 cm (measured from base of lowest flower to top of upper flower).
- *Diameter.*—Approximately 13.8 cm.
- *Peduncle.*—Dimensions — Approximately 57.2 cm long and 0.6 cm wide. Aspect — Approximately 60 degree angle to lateral branch axis. Strength — Moderately strong. Texture and luster — Glabrous and moderately glossy. Color — Brown, near RHS 200A yet darker.

Bud:

- *Length.*—Average of 1.8 cm.
- *Horizontal diameter.*—Average of 1.6 cm.
- *Vertical diameter.*—Average of 1.8 cm.
- *Shape.*—Broad obovate.

*Pubescence, texture and luster.*—Glabrous, smooth and slightly glossy.

*Color.*—Yellow-green, near RHS 151C to 151D; base is heavily tinged and blushed greyed-yellow, near RHS 185A and 185B; apex is black, near RHS 203C.

Flower:

*Flower type.*—Zygomorphic (orchidaceous), typical shape for the genus *Phalaenopsis*.

*Flowering habit.*—Moderate.

*Shape.*—Zygomorphic, single; consisting of three sepals and three petals, one of which is transformed into a labellum.

*Aspect.*—Flowers are outward-facing.

*Vertical height.*—Approximately 6.8 cm.

*Diameter.*—Approximately 8.3 cm.

*Depth.*—Approximately 2.8 cm.

*Fragrance.*—No fragrance.

*Lastingness.*—3 weeks.

*Persistent.*—Self-cleaning.

*Petals.*—Quantity of petals — 3 unfused petals; two conventional petals and one labellum. Arrangement — One lateral petal on each side. Length — Approximately 4.0 cm. Width — Approximately 5.8 cm. Shape — Reniform. Apex — Obtuse. Base — Cuneate. Margin — Irregular, finely dentate; no undulation to very little undulation. Pubescence, texture and luster of upper surface — Glabrous, velvety and matte. Pubescence, texture and luster of lower surface — Glabrous, velvety and matte. Color when opening, upper surface — White, near RHS NN155D; base is purple-violet, near RHS N80B to N80C; apex is greyed-purple, near RHS N186B; entire petal is irregularly dotted red-purple, RHS 59A to 59D. Color when opening, lower surface — White, near RHS NN155A, and tinged purple-violet, near RHS N80D yet lighter; base is purple, near RHS N78B to N78C; apex is greyed-purple, near RHS N186B. Color when fully opened, upper surface — White, near RHS NN155D; base is slightly tinged purple, near RHS N78C to N78D; apex is greyed-purple, near RHS N186C; entire petal is irregularly dotted red-purple, RHS 71A. Color when fully opened, lower surface — White, near RHS NN155C, and tinged purple-violet, near RHS N78C to N78D, especially towards the base; apex is greyed-purple, near RHS N186C. Fading, upper surface — Not fading. Fading, lower surface — Not fading. Venation color, fully opened, upper surface — White, near RHS NN155D; base is slightly tinged purple, near RHS N78C to N78D; apex is greyed-purple, near RHS N186C; entire petal is irregularly dotted red-purple, RHS 71A. Venation color, fully opened, lower surface — Purple-violet, near RHS N78C to N78D.

*Labellum.*—Shape — Three-lobed; lateral lobes are near orbicular and the central lobe is deltoid. Length — Central lobe — Approximately 3.8 cm. Lateral lobes — Approximately 2.0 cm. Width — Central lobe — Approximately 2.4 cm. Lateral lobes — Approximately 1.9 cm. Apex — Central lobe — Cleft, with tips curved upward. Lateral lobes — Obtuse. Base, central and lateral lobes — Cuneate. Margin, central and lateral lobes — Entire; central lobe slightly undulate and lateral lobes not undulate. Pubescence, texture and luster of upper surface — Glabrous, velvety, and matte. Pubescence, texture and luster of lower surface — Glabrous, velvety, and matte. Color when opening, upper surface — Central lobe — Red-purple, near RHS 59B and 60B, and lighter towards the apex, near RHS 71B and 71C; base of the cleft area is white, near RHS NN155D. Lateral lobes — Red-purple, near RHS 60A to 60B and 70A, and marbled white, RHS NN155A; base is red-purple, near RHS 59A to 59B, with a small yellow dot on the upper margin, near RHS 4B. Color when opening, lower surface — Central lobe — Red-purple, near 61A, and purple towards the apex, near RHS N78B and N78C; base of the cleft area is white, near RHS NN155C. Lateral lobes — Purple, near RHS N78C; base is white, RHS 155A, and marbled red-purple, near RHS 60A, with a small yellow dot on the upper margin, near RHS 4A. Color when fully opened, upper surface — Central lobe — Red-purple, near RHS 59B and 60B, and lighter towards the apex, near RHS 71 B and 71 C; base of the cleft area is white, near RHS NN155D. Lateral lobes — Red-purple, near RHS 60A to 60B and 72A, and marbled white, RHS NN155A; base is red-purple, near RHS 59A to 59B, with a small yellow dot on the upper margin, near RHS 4A. Color when fully opened, lower surface — Central lobe — Red-purple, near 61A, and purple towards the apex, near RHS N78B and N78C; base of the cleft area is white, near RHS NN155C. Lateral lobes — Purple, near RHS 77B; base is white, RHS NN155A to NN155B, and marbled red-purple, near RHS 60A, with a small yellow dot on the upper margin, near RHS 4A. Fading, upper surface — Not fading. Fading, lower surface — Not fading. Venation color, fully opened, upper surface — Central lobe — Red-purple, near RHS 59B and 60B, and lighter towards the apex, near RHS 71B and 71C; base of the cleft area is white, near RHS NN155D. Lateral lobes — Red-purple, near RHS 60A to 60B and 72A, and marbled white, RHS NN155A; base is red-purple, near RHS 59A to 59B, with a small yellow dot on the upper margin, near RHS 4A. Venation color, fully opened, lower surface — Central lobe — Red-purple, near 61A, and purple towards the apex, near RHS N78B and N78C; base of the cleft area is white, near RHS NN155C. Lateral lobes — Purple, near RHS 77B; base is white, RHS NN155A to NN155B, and marbled red-purple, near RHS 60A, with a small yellow dot on the upper margin, near RHS 4A.

*Callosities.*—Location — Centrally placed on the base of the central lobe of the labellum. Dimensions — Average of 0.5 cm long and 0.6 cm wide. Color — Yellow, near RHS 11 B, and heavily dotted greyed-purple, near RHS 185A.

*Spurs.*—None.

*Sepals.*—Quantity — Average of 3 unfused sepals. Arrangement — One dorsal sepal and two lateral sepals. Length — Dorsal sepal — Approximately 4.0 cm. Lateral sepals — Approximately 4.0 cm. Width — Dorsal sepal — Approximately 3.2 cm. Lateral sepals — Approximately 2.8 cm. Shape — Dorsal sepal — Obovate. Lateral sepals — Elliptical to ovate. Apex — Dorsal sepal — Obtuse. Lateral sepals — Broad acute. Base — Dorsal sepal —

Cuneate. Lateral sepals — Cuneate. Margin, dorsal and lateral sepals — Entire; no undulation. Pubescence, texture and luster — Glabrous, velvety, and matte on both the upper and lower sepal surfaces. Color when opening, upper surface — Dorsal sepal — White, RHS NN155A, and irregularly margined and occasionally dotted red-purple, near RHS 59A; apex is greyed-purple, near N186C, to black, near 202A. Lateral sepals — White, RHS NN155A, with the lower half yellow, RHS 4D, and irregularly margined and occasionally dotted red-purple, near RHS 59A; apex is greyed-purple, near N186C, to black, near 202A. Color when opening, lower surface — Dorsal sepal — Greyed-yellow, near RHS 160A to 160B and 162B, and margined greyed-purple, near N186C, to black, near 202A. Lateral sepals — Greyed-yellow, near RHS 160A to 160B and 162B, and margined greyed-purple, near N186C, to black, near 202A; base tinged red-purple, near RHS 60C. Color when fully opened, upper surface — Dorsal sepal — White, RHS NN155D, and irregularly margined and occasionally dotted red-purple, near RHS 64A; outer edge and apex are greyed-purple, near N186C; sepal with a broad central stripe of red-purple, RHS near 61A. Lateral sepals — White, RHS NN155D, with the lower half slightly darker, near RHS NN155B, and broadly margined and occasionally dotted red-purple, near RHS 64A; outer edge and apex are greyed-purple, near N186C. Color when fully opened, lower surface — Dorsal and lateral sepals — White, near RHS NN155D, and tinged purple, near RHS 75C and 75D, with a greyed-yellow spot, near 160B and 160C, slightly above the center; base strongly tinged red-purple, RHS N74C, and margined greyed-purple, near RHS N186C; apex is greyed-purple, near RHS N186C, to black, RHS 202A. Fading, upper surface — The color of all sepals does not fade. Fading, lower surface — The color of all sepals does not fade. Venation color, fully opened, upper surface — Dorsal sepal — White, RHS NN155D, and irregularly margined and occasionally dotted red-purple, near RHS 64A; sepal with a broad central stripe of red-purple, RHS near 61A. Lateral sepals — White, RHS NN155D, with the lower half slightly darker, near RHS NN155B, and broadly margined and occasionally dotted red-purple, near RHS 64A. Venation color, fully opened, lower surface — Dorsal and lateral sepals — Red-purple, RHS N74B to N74C.

*Pedicels*.—Length — Approximately 3.9 cm. Diameter — Approximately 0.3 cm. Angle — Approximately 50 degree angle to peduncle axis. Strength — Moderate. Pubescence, texture and luster — Glabrous, smooth and glossy. Color — Purple, near RHS 77C, and fading to greyed-orange, RHS 177B; brown, RHS N200B and N200C, towards the proximal end.

*Bract*.—Quantity — One small bract present at the base of each pedicel. Shape — Deltoid; folded around the base of each pedicel. Dimensions — Average of 0.5 cm long and 0.55 cm wide. Apex — Acute. Base — Broad Cuneate. Margins — Entire. Color, both surfaces — Greyed-purple, near RHS 183D.

Reproductive organs:

*Column*.—Length — Approximately 0.8 cm. Diameter — Approximately 0.7 cm. Color — White, RHS NN155D, and dotted purple, RNS N78B to N78C.

*Ovary*.—Position — Inferior Diameter — Approximately 0.5 cm. Color — Purple, near RHS 77C.

*Pollinia color*.—Orange RHS 26A.

Seed and fruit: No fruit and seed production has been detected to date.

Comparisons with the Parent Plants

Plants of the new cultivar 'Suphal1401' are similar to the seed parent, *Phalaenopsis* Blume 'G3S8', in most horticultural characteristics. However 'Suphal1401' differs from the seed parent in the following characteristics:

1. The flowers of 'Suphal1401' are larger than the flowers of 'G3S8'.
2. The flower color pattern of 'Suphal1401' differs from that of 'G3S8'.
3. The sepals and petals of 'Suphal1401' exhibit fewer color spots when compared to the sepals and petals of 'G3S8'.

Plants of the new cultivar 'Suphal1401' are similar to the pollen parent, *Phalaenopsis* Blume 'B4P', in most horticultural characteristics. However 'Suphal1401' differs from the pollen parent in the following characteristics:

1. The flowers of 'Suphal1401' exhibit clearer and better color when compared to the flowers of 'B4P'.
2. The flower color pattern of 'Suphal1401' differs from that of 'B4P'.
3. The sepals and petals of 'Suphal1401' exhibit more color spots when compared to the sepals and petals of 'B4P'.

Comparison with the Most Similar *Phalaenopsis* Cultivar Known to the Inventor 'Suphal1401' is similar to the commercial variety *Phalaenopsis* 'Suphal1119' (not patented in the United States; Community Plant Variety Rights grant number 34865) in many horticultural characteristics. However, 'Suphal1401' differs from 'Suphal1119' in the following characteristics:

1. The petal color of 'Suphal1401' consists of both dark and light purple spots and blotches of irregular size and arrangement against a white background which is tinged light violet, whereas the petal color pattern of 'Suphal1119' consists of dark red-purple spots which are somewhat uniformly sized and distributed across the petal against a white background.
2. The sepals and petals of 'Suphal1401' exhibit fewer color spots when compared to the sepals and petals of 'Suphal1119'.
3. The lateral sepal of 'Suphal1401' are shorter and more rounded when compared to the lateral sepals of 'Suphal1119'.
4. The dorsal sepal of 'Suphal1401' is shorter and more rounded when compared to the dorsal sepal of 'Suphal1119'.
5. The labellum of *Phalaenopsis* 'Suphal1401' exhibits a dark red-purple general tonality, whereas 'Suphal1119' exhibits a white labellum overlaid with a light red-purple color pattern and yellow intonations near the base of each lobe.

That which is claimed is:

1. A new and distinct variety of *Phalaenopsis* plant named 'Suphal1401', substantially as described and illustrated herein.

* * * * *